(12) United States Patent
Su et al.

(10) Patent No.: US 10,095,000 B2
(45) Date of Patent: Oct. 9, 2018

(54) SINGLE-MODE OPTICAL FIBER HAVING AUTOMATIC CONTROL HEAT SOURCE SPECIFICALLY PRODUCED FOR HYDRAULIC SEEPAGE MEASUREMENT

(71) Applicant: HOHAI UNIVERSITY, Nanjing, Jiangsu (CN)

(72) Inventors: Huaizhi Su, Jiangsu (CN); Meng Yang, Jiangsu (CN)

(73) Assignee: HOHAI UNIVERSITY, Nanjing, Jiangsu (CN)

( * ) Notice: Subject to any disclaimer, the term of this patent is extended or adjusted under 35 U.S.C. 154(b) by 0 days.

(21) Appl. No.: 15/736,080

(22) PCT Filed: Jan. 11, 2016

(86) PCT No.: PCT/CN2016/070585
§ 371 (c)(1),
(2) Date: Dec. 13, 2017

(87) PCT Pub. No.: WO2016/201969
PCT Pub. Date: Dec. 22, 2016

(65) Prior Publication Data
US 2018/0188467 A1      Jul. 5, 2018

(30) Foreign Application Priority Data
Jun. 19, 2015   (CN) .......................... 2015 1 0345133 7

(51) Int. Cl.
*G02B 6/44* (2006.01)
*G01D 5/26* (2006.01)

(52) U.S. Cl.
CPC ........... *G02B 6/4494* (2013.01); *G01D 5/268* (2013.01); *G02B 6/4436* (2013.01); *G02B 6/4402* (2013.01)

(58) Field of Classification Search
None
See application file for complete search history.

(56) References Cited

U.S. PATENT DOCUMENTS 4,957,345 A * 9/1990 Sakuma ............... G02B 6/4436
385/103
5,487,126 A * 1/1996 Oestreich ............. G02B 6/4403
242/444

(Continued)

FOREIGN PATENT DOCUMENTS

CN     2669186      1/2005
CN     104515653    4/2015

(Continued)

OTHER PUBLICATIONS

English translation of written opinion for PCT/CN2016/070585, dated Apr. 8, 2016.*

(Continued)

*Primary Examiner* — Mike Stahl
(74) *Attorney, Agent, or Firm* — Rankin, Hill & Clark LLP

(57) ABSTRACT

A single-mode optical fiber having an automatic control heat source specifically produced for hydraulic seepage measurement, sequentially includes a single-core optical fiber, an inner protective elastic layer, a heat insulation steel ring, an inner-layer filling protection ring, an elastic hard ring, and an anti-seepage heat insulation hard sleeve ring arranged from inside to outside. The single-core optical is connected to a plurality of outer circular sheathing protection pipes respectively, the outer circular sheathing protection pipes sequentially pass through the inner protective elastic layer, the heat insulation steel ring, the inner-layer filling protection ring and the elastic hard ring and are connected to the anti-seepage heat insulation hard sleeve ring, each outer circular sheathing protection pipe is filled with a drainage water (Continued)

storage cotton sleeve, the drainage water storage cotton sleeve is connected to a second filter screen, and the second filter screen is connected to a first filter screen externally.

5 Claims, 2 Drawing Sheets

(56) References Cited

U.S. PATENT DOCUMENTS

| | | |
|---|---|---|
| 7,936,957 B1 | 5/2011 | Puzan et al. |
| 2007/0081773 A1 | 4/2007 | Pizzorno |

FOREIGN PATENT DOCUMENTS

| | | |
|---|---|---|
| CN | 104570148 | 4/2015 |
| CN | 204287517 | 4/2015 |
| CN | 204330232 | 5/2015 |
| CN | 104977233 | 10/2015 |
| CN | 104977673 | 10/2015 |
| CN | 204789261 | 11/2015 |
| CN | 204790103 | 11/2015 |

OTHER PUBLICATIONS

International Search Report filed in PCT/CN2016/070585 dated Apr. 8, 2016.

* cited by examiner

SINGLE-MODE OPTICAL FIBER HAVING AUTOMATIC CONTROL HEAT SOURCE SPECIFICALLY PRODUCED FOR HYDRAULIC SEEPAGE MEASUREMENT

TECHNICAL FIELD

The present invention relates to a single-mode optical fiber, and more particularly, to a single-mode optical fiber having an automatic control heat source specifically produced for hydraulic seepage measurement.

BACKGROUND

The naissance of optical fibers not only brings innovation to the field of communications, but also contributes to major revolutions and development in the field of sensor monitoring. The technical superiorities of an optic sensing technology like resistance to strong electromagnetic interference, low cost, and distributed monitoring promote it to be widely used in the field of safety and health monitoring such as water conservancy and civil engineering. However, due to the incomplete technology itself and the specificity of the working environment, there are still a large number of technical problems which have not been effectively resolved to apply the optical fiber sensing technology in hydraulic structure seepage monitoring (especially seepage quantity and seepage line monitoring). Although a conventional optimal design by means of optical fiber layout plans plays a certain positive role of improving the optical fiber seepage measurement accuracy and efficiency, the technical defects and deficiencies of conventional optical fiber seepage measurement cannot be fundamentally solved yet; moreover, the construction difficulty and layout cost will be significantly increased usually, which greatly limits the application and promotion of the technology in actual engineering.

When sensing optical fiber is used for seepage monitoring, an external circuit is usually needed to heat the optical fiber; for this purpose, not only the optical fiber used needs to have a heating function, but also a complete heating circuit needs to be built, which greatly increases the production cost of the optical fiber. Moreover, since it is difficult to coordinate a relationship between the external circuit and the heating optical fiber during indoor and outdoor monitoring, voltage instability or too large heating optical fiber is frequently caused, and a jacket of the optical fiber is soft or even burned in a short time therefore, which causes severe harm to operators and instruments. In addition, on-site monitoring applied to actual engineering often lacks necessary safety measures, and it is difficult to lay the heating circuits. It is more difficult and even unable to implement optical fiber laying and heating function since most of water conservancy and hydropower engineering are located in remote areas with very bad construction and operation environments. Therefore, it is urgent to fully consider the characteristics of hydraulic seepage monitoring and special working environment, focus on the production and assembly of the sensing optical fiber itself, and develop an optical fiber having an automatic control heat source specifically produced for hydraulic seepage measurement, so as to enhance the performance indicators and practical ability of the optical fiber seepage measurement technology from the source.

The present invention is just developed on the basis of the above-mentioned background and object and with reference to the problems encountered in practical engineering. The single-core arrangement of the present invention can detect structure seepage more effectively and directly, so that the application range of the present invention can be further expanded. The five-layer arrangement of the inner protective elastic layer, the heat insulation steel ring, the inner-layer filling protection ring, the elastic hard ring and the anti-seepage heat insulation hard sleeve ring increases the levels of anti-seepage and elastic buffer, and has stronger engineering suitability. The inwards depressed design of the four sides greatly increases the monitoring directions and scope of the present invention. The simple design of the drainage water storage cotton sleeve, the first filter screen and the second filter screen enhances the entire adaptation of the present invention.

SUMMARY

Object of the Invention in order to overcome the defects in the prior art, the present invention provides a single-mode optical fiber having an automatic control heat source specifically produced for hydraulic seepage measurement. In the present invention, an anti-seepage heat insulation hard sleeve ring can isolate a structure at the position with four sides depressed inwards excluding a filter screen, and prevent seepage; seepage water is filtered under the joint action of a gauze of a first filter screen and a gauze of a second filter screen; moreover, the gauze of the first filter screen and the gauze of the second filter screen are provided with through-holes having different diameters, which can control the flow of the seepage water; and the seepage water with controlled seepage rate after passing through a drainage water storage cotton sleeve is contacted with a single-core optical fiber; the contact between the seepage water under different flow rates and the single-core optical fiber implements the automatic temperature changing; when external seepage is larger, the seepage flow rate of the seepage water is larger, then the contact speed with the single-core optical fiber is faster, and the temperature is reduced more quickly in a short time; on the contrary, the temperature is reduced more slowly.

Technical Solution

In order to achieve the above-mentioned object, a single-mode optical fiber having an automatic control heat source specifically produced for hydraulic seepage measurement according to the present invention comprises a single-core optical fiber, an inner protective elastic layer, a heat insulation steel ring, an inner-layer filling protection ring, an elastic hard ring, and an anti-seepage heat insulation hard sleeve ring arranged in sequence from inside to outside. The single-core optical fiber is connected to a plurality of outer circular sheathing protection pipes respectively, the outer circular sheathing protection pipes sequentially pass through the inner protective elastic layer, the heat insulation steel ring, the inner-layer filling protection ring and the elastic hard ring and are connected to the anti-seepage heat insulation hard sleeve ring, each outer circular sheathing protection pipe is filled with a drainage water storage cotton sleeve, the drainage water storage cotton sleeve is connected to a second filter screen, the second filter screen is provided with a gauze through-hole of the second filter screen, the second filter screen is connected to a first filter screen externally, and the first filter screen is provided with a gauze through-hole of the first filter screen.

Preferably, the elastic hard ring and the anti-seepage heat insulation hard sleeve ring are irregular quadrilateral frames, the four sides of the quadrilateral frame are depressed inwards, and the four corners of the quadrilateral frame are round corners, which can be better meshed with a structure to be measured, so as to implement cooperative deformation.

Preferably, the aperture of the gauze through-hole of the first filter screen arranged on the first filter screen is greater than the aperture of the gauze through-hole of the second filter screen arranged on the second filter screen, and the difference of the aperture of the two gauze through-holes is more than two times.

Preferably, four outer circular sheathing protection pipes are arranged, and respectively located on 0-degree, 90-degree, 180-degree and 270-degree radix directions of the single-core optical fiber.

Preferably, both the first filter screen and the second filter screen are located inside the anti-seepage heat insulation hard sleeve ring.

The single-core optical fiber in the present invention can detect structure seepage water more effectively and directly, so that the application range of the present invention can be further expanded. Moreover, the present invention is convenient to be produced, and the five-layer arrangement of the inner protective elastic layer, the heat insulation steel ring, the inner-layer filling protection ring, the elastic hard ring and the anti-seepage heat insulation hard sleeve ring increases the levels of anti-seepage and elastic buffer, and has stronger engineering suitability.

The inwards depressed design of the four sides greatly adopted in the present invention increases the monitoring directions and scope of the present invention, and can implement multiaspect monitoring like 0-degree, 90-degree, 180-degree and 270-degree monitoring. In order to better support multiaspect monitoring, the drainage water storage cotton sleeve, the first filter screen and the second filter screen in the corresponding directions are designed, which are easy to manufacture, and enhances the entire adaptation of the present invention since the drainage water storage cotton sleeve, the first filter screen and the second filter screen are only connected to the single-mode optical fiber.

In the present invention, the anti-seepage heat insulation hard sleeve ring can isolate a structure at the position with four sides depressed inwards excluding a filter screen, and prevent seepage; seepage water is filtered under the joint action of the gauze of the first filter screen and the gauze of the second filter screen; moreover, the gauze of the first filter screen and the gauze of the second filter screen are provided with through-holes having different diameters, which can control the flow of the seepage water; and the seepage water with controlled seepage rate after passing through a drainage water storage cotton sleeve is contacted with the single-core optical fiber; the contact between the seepage water under different flow rates and the single-core optical fiber implements the automatic temperature changing; when external seepage is larger, the seepage flow rate of the seepage water is larger, then the contact speed with the single-core optical fiber is faster, and the temperature is reduced more quickly in a short time; on the contrary, the temperature is reduced more slowly. The present invention can implement automatic temperature changing on the basis of external actual seepage situations Beneficial Effects The single-mode optical fiber having an automatic control heat source specifically produced for hydraulic seepage measurement according to the present invention can implement automatic temperature changing of the single-core optical fiber by arranging the inner protective elastic layer, the heat insulation steel ring, the inner-layer filling protection ring, the elastic hard ring and the anti-seepage heat insulation hard sleeve ring outside the single-core optical fiber, and a great temperature difference is formed between the single-core optical fiber and the environment; when the single-mode optical fiber is applied to seepage monitoring, the seepage identification level and the practicality can be significantly improved.

In the figures, 200 refers to third transition protrusion end, 201 refers to outer circular sheathing protection pipe, 202 refers to second transition protrusion end, 203 refers to first transition protrusion end, 204 refers to gauze through-hole of first filter screen, 205 refers to first filter screen, 206 refers to second filter screen, 207 refers to gauze through-hole of second filter screen, 208 refers to drainage water storage cotton sleeve, 209 refers to heat insulation steel ring, 201 refers to inner protective elastic layer, 211 refers to single-core optical fiber, 212 refers to inner-layer filling protection ring, 213 refers to elastic hard ring, and 214 refers to anti-seepage heat insulation hard sleeve ring.

DETAILED DESCRIPTION

The present invention is further explained with reference to the drawings hereinafter.

Figure 1:
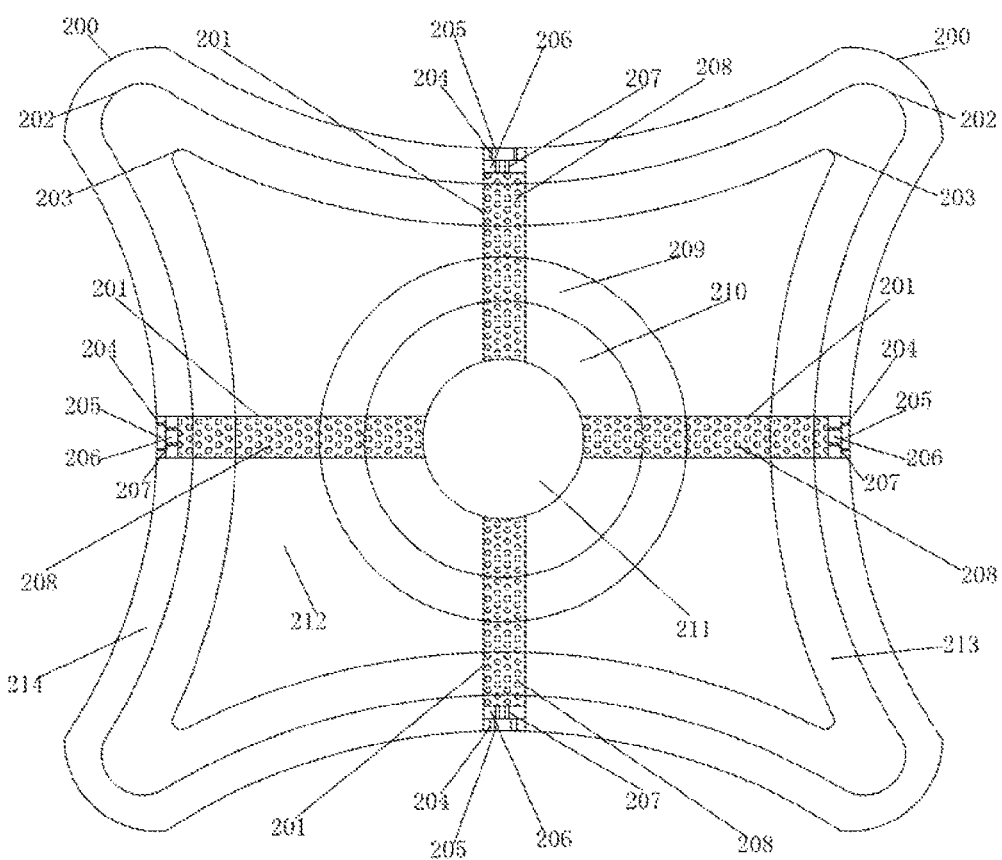
FIG. 1 is a structural schematic diagram of the present invention.
Figure 2:
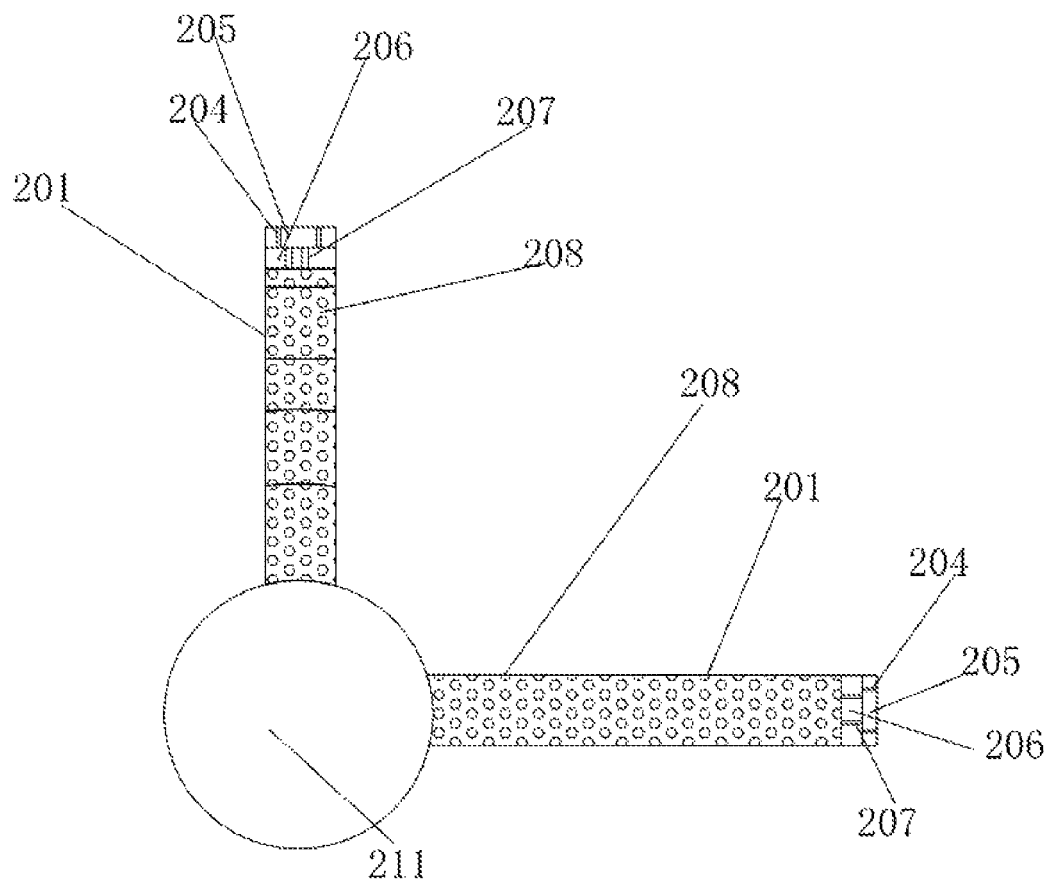
FIG. 2 is a structural schematic diagram of outer circular sheathing protection pipes in FIG. 1.

As shown in FIG. 1 and FIG. 2, a single-mode optical fiber having an automatic control heat source specifically produced for hydraulic seepage measurement according to the present invention is provided with a single-core optical fiber 211, an inner protective elastic layer 210, a heat insulation steel ring 209, an inner-layer filling protection ring 212, an elastic hard ring 213 and an anti-seepage heat insulation hard sleeve ring 214 in sequence from inside to outside. The single-core optical fiber 211 is respectively connected to four outer circular sheathing protection pipes 201 which are respectively located on 0-degree, 90-degree, 180-degree and 270-degree radical directions of the single-core optical fiber 211. The outer circular sheathing protection pipes 201 sequentially pass through the inner protective elastic layer 210, the heat insulation steel ring 209, the inner-layer filling protection ring 212 and the elastic hard ring 213 and are connected to the anti-seepage heat insulation hard sleeve ring 214, each outer circular sheathing protection pipe 201 is filled with a drainage water storage cotton sleeve 208, the drainage water storage cotton sleeve 208 mainly leads seepage water filtered by a first filter screen 205 and a second filter screen 206 onto the single-core optical fiber and stores the seepage water in the cotton sleeve transitorily. The first filter screen 205 and the second filter screen 206 mainly filter the seepage water to remove impurities in the seepage water. An aperture-variable through-hole design may implement to control the seepage flow rate. The drainage water storage cotton sleeve 208 is connected to the second filter screen 206, the second filter screen 206 is provided with a gauze through-hole 207 of the second filter screen, the second filter screen 206 is connected to the first filter screen 205 externally, and the first filter screen 205 is provided with a gauze through-hole 204 of the first filter screen. The inner protective elastic layer 210 is made of a TPE thermoplastic elastomer, the heat insulation steel ring 209 is made of Q345 low alloy steel, the inner-layer filling protection ring 212 is made of a linear low density polyethylene material, the elastic hard ring 213 is made of a polyester elastomer material, and the anti-seepage heat insulation hard sleeve ring 214 is a structure composed of materials such as polyacrylic acid, magnesium oxide, sodium silicate, stearic acid, aluminum dihydrogen phosphate, etc.

The inner protective elastic layer 210 is mainly contacted with the single-core optical fiber directly to play a role of buffering and protecting the optical fiber. The heat insulation steel ring 209 blocks heat outside the inner protective elastic layer 210 in the outside and protects the inner protective elastic layer 210. The inner-layer filling protection ring 212 mainly fills in the blank between the heat insulation steel ring 209 and the elastic hard ring 213 to make the structure be more tightly sealed. The elastic hard ring 213 plays a role of connection and secondary protection, which connects the inner-layer filling protection ring 212 with the anti-seepage heat insulation hard sleeve ring 214, and protects the internal components from damage. The anti-seepage heat insulation hard sleeve ring 214 mainly plays a role of preventing outside water from infiltration and blocking the transfer of external heat.

In the present invention, the elastic hard ring 213 and the anti-seepage heat insulation hard sleeve ring 214 are irregular quadrilateral frames, the four sides of the quadrilateral frame are depressed inwards, and the four corners of the quadrilateral frame are round corners, which are respectively a third transition protrusion end 200, a second transition protrusion end 202, and a first transition protrusion end 203 formed by the anti-seepage heat insulation hard sleeve ring 214, the elastic hard ring 213 and the inner-layer filling protection ring 212. The aperture of the gauze through-hole 204 of the first filter screen arranged on the first filter screen 205 is greater than the aperture of the gauze through-hole 207 of the second filter screen arranged on the second filter screen 206, and the difference of the aperture of the two gauze through-holes is more than two times. Both the first filter screen 205 and the second filter screen 206 are located in the anti-seepage heat insulation hard sleeve ring 214.

Those described above are merely preferred embodiments of the invention It should be noted that, those having ordinary skills in the art can make a plurality of improvements and modifications without departing from the principle of the invention, and those improvements and modifications all fall in the scope of protection of the invention.

The invention claimed is:

1. A single-mode optical fiber having an automatic control heat source specifically produced for hydraulic seepage measurement, comprising: a single-core optical fiber, an inner protective elastic layer, a heat insulation steel ring, an inner-layer filling protection ring, an elastic hard ring, and an anti-seepage heat insulation hard sleeve ring arranged in sequence from inside to outside, wherein the single-core optical fiber is connected to a plurality of outer circular sheathing protection pipes respectively, the outer circular sheathing protection pipes sequentially pass through the inner protective elastic layer, the heat insulation steel ring, the inner-layer filling protection ring and the elastic hard ring and are connected to the anti-seepage heat insulation hard sleeve ring, each outer circular sheathing protection pipe is filled with a drainage water storage cotton sleeve, the drainage water storage cotton sleeve is connected to a second filter screen, the second filter screen is provided with a gauze through-hole of the second filter screen, the second filter screen is connected to a first filter screen externally, and the first filter screen is provided with a gauze through-hole of the first filter screen.

2. The single-mode optical fiber having an automatic control heat source specifically produced for hydraulic seepage measurement according to claim 1, wherein the elastic hard ring and the anti-seepage heat insulation hard sleeve ring are irregular quadrilateral frames, the four sides of the quadrilateral frame are depressed inwards, and the four corners of the quadrilateral frame are round corners.

3. The single-mode optical fiber having an automatic control heat source specifically produced for hydraulic seepage measurement according to claim 2, wherein the aperture of the gauze through-hole of the first filter screen arranged on the first filter screen is larger than the aperture of the gauze through-hole of the second filter screen arranged on the second filter screen, and a difference in size of the apertures of the two gauze through-holes is more than two times.

4. The single-mode optical fiber having an automatic control heat source specifically produced for hydraulic seepage measurement according to claim 3, wherein four outer circular sheathing protection pipes are arranged, and respectively located on 0-degree, 90-degree, 180-degree and 270-degree radix directions of the single-core optical fiber.

5. The single-mode optical fiber having an automatic control heat source specifically produced for hydraulic seepage measurement according to claim 4, wherein both the first filter screen and the second filter screen are located inside the anti-seepage heat insulation hard sleeve ring.

* * * * *